(12) United States Patent
Bruehwiler et al.

(10) Patent No.: US 8,096,964 B1
(45) Date of Patent: Jan. 17, 2012

(54) COMPRESSION GARMENT HAVING GRIP

(75) Inventors: Michel Bruehwiler, Newton, MA (US); Melissa Rosen, Salem, MA (US); Manish Deshpande, Canton, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/893,694

(22) Filed: Sep. 29, 2010

(51) Int. Cl.
*A61F 5/00* (2006.01)

(52) U.S. Cl. ............................ 602/13; 602/20; 602/23

(58) Field of Classification Search ............. 602/13, 602/20, 21–27; 128/DIG. 20
See application file for complete search history.

(56) References Cited

U.S. PATENT DOCUMENTS

| | | |
|---|---|---|
| 3,703,171 A | 11/1972 | Schiavitto |
| 3,853,123 A | 12/1974 | Moore |
| 3,868,952 A | 3/1975 | Hatton |
| 3,935,858 A | 2/1976 | Harroff |
| 4,013,070 A | 3/1977 | Harroff |
| 4,090,508 A | 5/1978 | Gaylord, Jr. |
| 4,215,687 A | 8/1980 | Shaw |
| 4,219,892 A | 9/1980 | Rigdon |
| 4,280,489 A | 7/1981 | Johnson, Jr. |
| 4,320,746 A | 3/1982 | Arkans et al. |
| 4,353,362 A | 10/1982 | DeMarco |
| 4,379,463 A | 4/1983 | Meier et al. |
| 4,388,920 A | 6/1983 | Hajost et al. |
| 4,402,312 A | 9/1983 | Villari et al. |
| 4,442,834 A | 4/1984 | Tucker et al. |
| 4,547,919 A | 10/1985 | Wang |
| 4,870,956 A | 10/1989 | Fatool et al. |
| 5,146,932 A * | 9/1992 | McCabe .................. 128/873 |
| 5,230,695 A | 7/1993 | Silver et al. |
| 5,254,122 A | 10/1993 | Shaw |
| 5,277,697 A | 1/1994 | France et al. |
| 5,316,547 A | 5/1994 | Gildersleeve |
| 5,334,135 A | 8/1994 | Grim et al. |
| 5,378,224 A | 1/1995 | Billotti |
| 5,385,538 A | 1/1995 | Mann |
| 5,393,303 A | 2/1995 | Shiono |
| 5,399,153 A | 3/1995 | Caprio, Jr. et al. |
| 5,415,625 A | 5/1995 | Cassford et al. |
| 5,450,858 A | 9/1995 | Zablotsky et al. |
| 5,462,517 A | 10/1995 | Mann |
| 5,520,622 A | 5/1996 | Bastyr et al. |
| 5,554,105 A | 9/1996 | Taylor |
| 5,558,627 A | 9/1996 | Singer et al. |
| 5,621,514 A | 4/1997 | Paranto et al. |
| 5,626,557 A | 5/1997 | Mann |
| 5,653,244 A | 8/1997 | Shaw |
| 5,730,710 A | 3/1998 | Eichhorn et al. |
| 5,795,312 A * | 8/1998 | Dye ........................ 601/151 |
| 5,797,851 A | 8/1998 | Byrd |
| 5,897,518 A | 4/1999 | Shaw |

(Continued)

*Primary Examiner* — Michael A. Brown
(74) *Attorney, Agent, or Firm* — Thomas M. Johnston, Esq.

(57) ABSTRACT

A compression garment adapted for placement in a self-retaining configuration on a body part for imparting compression therapy on the body part. The compression garment includes a flexible wrap and a bladder held in use by the wrap for compressing the body part. The wrap includes and inner flap and an outer flap. The outer flap overlaps the inner flap when the garment is in a self-retaining configuration on the body part. A fastener secures the wrap in the self-retaining configuration. When the outer flap overlaps the inner flap, at least a portion of the inner flap is exposed forming a grip for grasping the inner flap when tightening and fastening the garment in the self-retaining configuration.

19 Claims, 4 Drawing Sheets

U.S. PATENT DOCUMENTS

| | | | |
|---|---|---|---|
| 5,906,206 A | 5/1999 | Shaw et al. |
| 5,916,183 A | 6/1999 | Reid |
| 5,918,602 A | 7/1999 | Shaw et al. |
| 5,993,405 A | 11/1999 | Wynn |
| 6,080,120 A | 6/2000 | Sandman et al. |
| 6,126,683 A | 10/2000 | Momtaheni |
| 6,152,893 A | 11/2000 | Pigg et al. |
| 6,190,344 B1 | 2/2001 | Bobroff |
| 6,287,269 B1 | 9/2001 | Osti et al. |
| 6,402,879 B1 | 6/2002 | Tawney et al. |
| 6,448,643 B2 | 9/2002 | Cheah et al. |
| 6,506,175 B1 | 1/2003 | Goldstein |
| 6,511,449 B2 | 1/2003 | Burns et al. |
| 6,682,547 B2 | 1/2004 | McEwen et al. |
| 6,974,433 B2 | 12/2005 | Hess |
| 7,011,640 B2 | 3/2006 | Patterson et al. |
| 7,083,586 B2 | 8/2006 | Simmons et al. |
| 7,217,249 B2 | 5/2007 | Scott |
| 7,258,676 B2 | 8/2007 | Calderon et al. |
| 7,276,037 B2 | 10/2007 | Ravikumar |
| 7,276,039 B2 | 10/2007 | Garelick et al. |
| 7,278,980 B1 | 10/2007 | Garelick et al. |
| 7,306,568 B2 | 12/2007 | Diana |
| 7,329,232 B2 * | 2/2008 | Lipshaw et al. ............... 602/61 |
| 7,354,410 B2 * | 4/2008 | Perry et al. ............... 601/151 |
| 7,354,411 B2 | 4/2008 | Perry et al. |
| 7,442,175 B2 | 10/2008 | Meyer et al. |
| 7,591,796 B1 | 9/2009 | Barak et al. |
| 7,591,797 B2 | 9/2009 | Hakonson et al. |
| 7,625,350 B2 | 12/2009 | Hunter et al. |
| 7,637,879 B2 | 12/2009 | Barak et al. |
| 7,749,182 B2 | 7/2010 | Gramza et al. |
| 7,758,607 B2 | 7/2010 | McEwen et al. |
| 7,780,698 B2 | 8/2010 | McEwen et al. |
| 7,862,527 B2 | 1/2011 | Gramza et al. |
| 2002/0068886 A1 | 6/2002 | Lin |
| 2006/0189907 A1 | 8/2006 | Pick et al. |
| 2007/0038167 A1 | 2/2007 | Tabron et al. |
| 2007/0135835 A1 | 6/2007 | McEwen et al. |
| 2007/0135836 A1 | 6/2007 | McEwen et al. |
| 2007/0161933 A1 | 7/2007 | Ravikumar |
| 2007/0167892 A1 | 7/2007 | Gramza et al. |
| 2008/0086071 A1 | 4/2008 | Weatherly |
| 2008/0103397 A1 | 5/2008 | Barak |
| 2008/0249440 A1 | 10/2008 | Avitable et al. |
| 2008/0249441 A1 | 10/2008 | Avitable et al. |
| 2008/0249442 A1 | 10/2008 | Brown et al. |
| 2008/0249443 A1 | 10/2008 | Avitable et al. |
| 2008/0249444 A1 | 10/2008 | Avitable et al. |
| 2008/0249449 A1 | 10/2008 | Brown et al. |
| 2008/0249455 A1 | 10/2008 | Brown et al. |
| 2008/0249559 A1 | 10/2008 | Brown et al. |
| 2009/0024062 A1 | 1/2009 | Einarsson |
| 2009/0124944 A1 | 5/2009 | Ravikumar |
| 2009/0177222 A1 | 7/2009 | Brown et al. |
| 2009/0234265 A1 | 9/2009 | Reid, Jr. et al. |
| 2009/0326576 A1 | 12/2009 | Ben-Nun |
| 2010/0004575 A1 | 1/2010 | Vess |
| 2010/0081974 A1 | 4/2010 | Vess |
| 2010/0081977 A1 | 4/2010 | Vess |

\* cited by examiner

COMPRESSION GARMENT HAVING GRIP

FIELD OF THE INVENTION

The present invention generally relates to a compression garment, and more particularly to a compression garment having a grip for facilitating application of the garment to a body part.

BACKGROUND OF THE INVENTION

A major concern for generally immobile patients and like persons are medical conditions that form blood clots, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popliteal, and tibial return deoxygenated blood to the heart. For example, when blood circulation in these veins is retarded due to illness, injury, or inactivity, there is a tendency for blood to accumulate or pool. A static pool of blood may lead to the formation of a blood clot, which can interfere with cardiovascular circulation. Most seriously, a fragment of the blood clot can break loose and migrate. A pulmonary embolus can form from the fragment potentially blocking a main pulmonary artery, which may be life threatening. The current invention can also be applied to the treatment of other conditions, such as lymphedema.

Conventional vascular compression systems include a compression garment fluidly connected to a controller for cyclically inflating the compression garment. The cyclical inflation of the compression garment enhances blood circulation and decreases the likelihood of DVT. A system of conduits connects the compression garment to the controller. Newer vascular compression garments have portable controllers that are much smaller and even mountable on the compression garment so that the patient may move about freely without having to first remove the compression garment or disconnect the compression garment from a controller. These new compression garments may be worn when a patient is stationary or ambulatory and enhance patient compliance because of convenience of use.

Active compression garments for applying intermittent compression therapy to a body part (e.g., a limb such as a leg) have many applications, including DVT prophylaxis, edema prevention, and aiding in wound healing. The performance of such compression garments is sensitive to the initial fit or tightness of the garment, the ability of the garment to retain its fit and tightness, and the ability of the inflatable bladders to retain their original position around the body part. This can be very difficult when the compression garments are used during and after ambulation, such as walking, sitting, standing, and rolling over. The garments tend to slide down the body part causing misalignment of inflatable bladders with corresponding body parts, which may result in ineffective compression therapy and/or discomfort. The present invention is directed to facilitating application of the garment to a body part to obtain a desired fit to improve applied compression therapy.

SUMMARY OF THE INVENTION

One aspect of the present invention is directed to a compression garment adapted for placement on a body part in a self-retaining configuration for providing compression therapy to the body part. The compression garment includes a flexible wrap having a proximal end sized for wrapping around a proximal portion of the body part, a distal end opposite the proximal end for wrapping around a distal portion of the body part, and side edges extending between the proximal end and the distal end. The compression garment also includes a bladder held in use by the wrap for compressing the body part. The bladder has an inflatable chamber and a port in fluid communication with the chamber for selectively delivering fluid from a fluid source to the chamber to inflate the chamber and compress the body part. An inner flap extends from one of the side edges and an outer flap extending from another of the side edges, the outer flap overlapping the inner flap when the garment is in use on the body part. A fastener is attached to at least one of the inner flap and the outer flap for securing the wrap in the self-retaining configuration on the body part in which the proximal end is wrapped around the proximal portion of the body part, the distal end is wrapped around the distal portion of the body part, and the outer flap overlaps the inner flap. The inner flap has a length extending from the respective side edge of the wrap to a free end and a maximum width measured generally perpendicular to a median circumferential centerline of the inner flap. The outer flap has a length extending from the respective side edge of the wrap to a free end, a maximum width measured generally perpendicular to a median circumferential centerline of the outer flap that is at least about half as wide as the maximum width of the inner flap, and a minimum width measured generally perpendicular to the median circumferential centerline of the outer flap that is less than the maximum width of the inner flap so that a portion of the inner flap is exposed when the proximal end is wrapped around the proximal portion of the body part, the distal end is wrapped around the distal portion of the body part, and the outer flap overlaps the inner flap forming a grip for grasping the inner flap when fastening the fastener to secure the wrap in the self-retaining configuration on the body part.

Another aspect of the invention is directed to a compression garment adapted for placement in a self-retaining configuration on a body part for imparting compression therapy on the body part. The compression garment includes a flexible wrap having a proximal end sized for wrapping around a proximal portion of the body part, a distal end opposite the proximal end for wrapping around a distal portion of the body part, and first and second side edges extending between the proximal end and the distal end. A bladder is held in use by the wrap for compressing the body part. The bladder has an inflatable chamber and a port in fluid communication with the chamber for selectively delivering fluid from a fluid source to the chamber to inflate the chamber to compress the body part. An inner flap extends from one of the side edges and an outer flap extending from another of the side edges. The outer flap overlaps the inner flap when the garment in use on the body part. A fastener is attached to at least one of the inner flap and the outer flap for securing the wrap in the self-retaining configuration on the body part in which the proximal end is wrapped around the proximal portion of the body part, the distal end is wrapped around the distal portion of the body part, and the outer flap overlaps the inner flap. The inner flap has a length extending from the respective side edge of the wrap to a free end and a maximum width measured generally perpendicular to a median circumferential centerline of the inner flap. The outer flap has a length extending from the respective side edge of the wrap to a free end, a maximum width measured generally perpendicular to a median circumferential centerline of the outer flap that is at least about half as wide as the maximum width of the inner flap, and a neck having a width less than the maximum width of the outer flap. The maximum width of the outer flap is positioned on the outer flap closer to the free end than the neck is positioned such that when the outer flap overlaps the inner flap at least a portion of the inner flap is not overlapped by the outer flap and is accessible adjacent the neck to facilitate gripping of the inner flap by fingers of a person to tighten the wrap about the body part.

Another aspect of the invention is directed to a method of placing a compression garment on a body part for providing compression therapy to the body part. The compression garment includes a bladder having an inflatable chamber and a port for providing fluid to the inflatable chamber. The method includes wrapping the compression garment around the body part such that an inner flap of the compression garment is overlapped by an outer flap of the compression garment and gripping the inner flap by grasping a portion of the inner flap. While gripping the inner flap, the overlap of the outer flap with respect to the inner flap is increased to tighten the compression garment around the body part. The outer flap is secured to the inner flap when the garment is tightened around the body part and without overlapping the grip with the outer flap.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
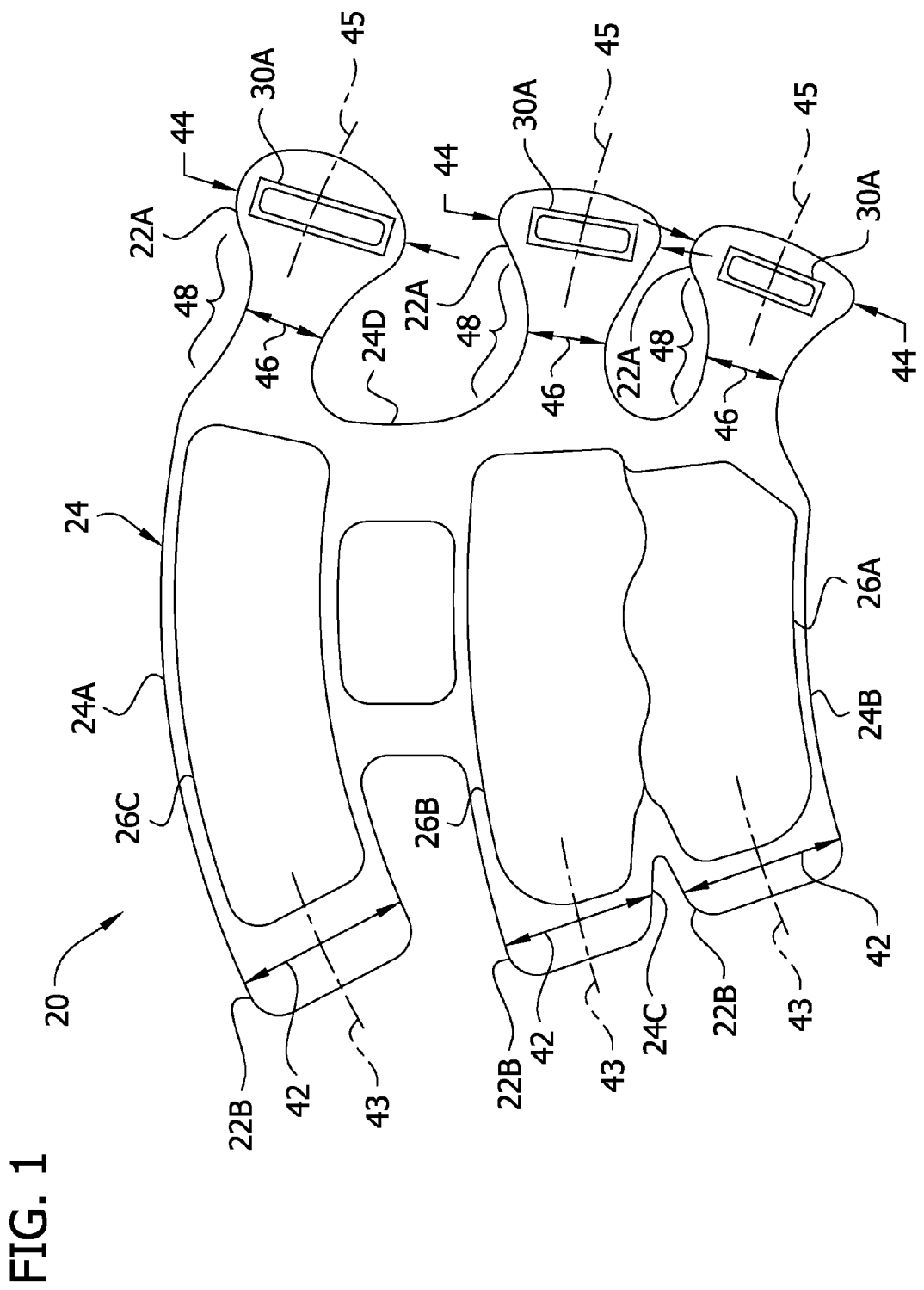
FIG. 1 is a schematical front elevation of a compression garment of the present invention shown in an open, unwrapped configuration.
Figure 2:
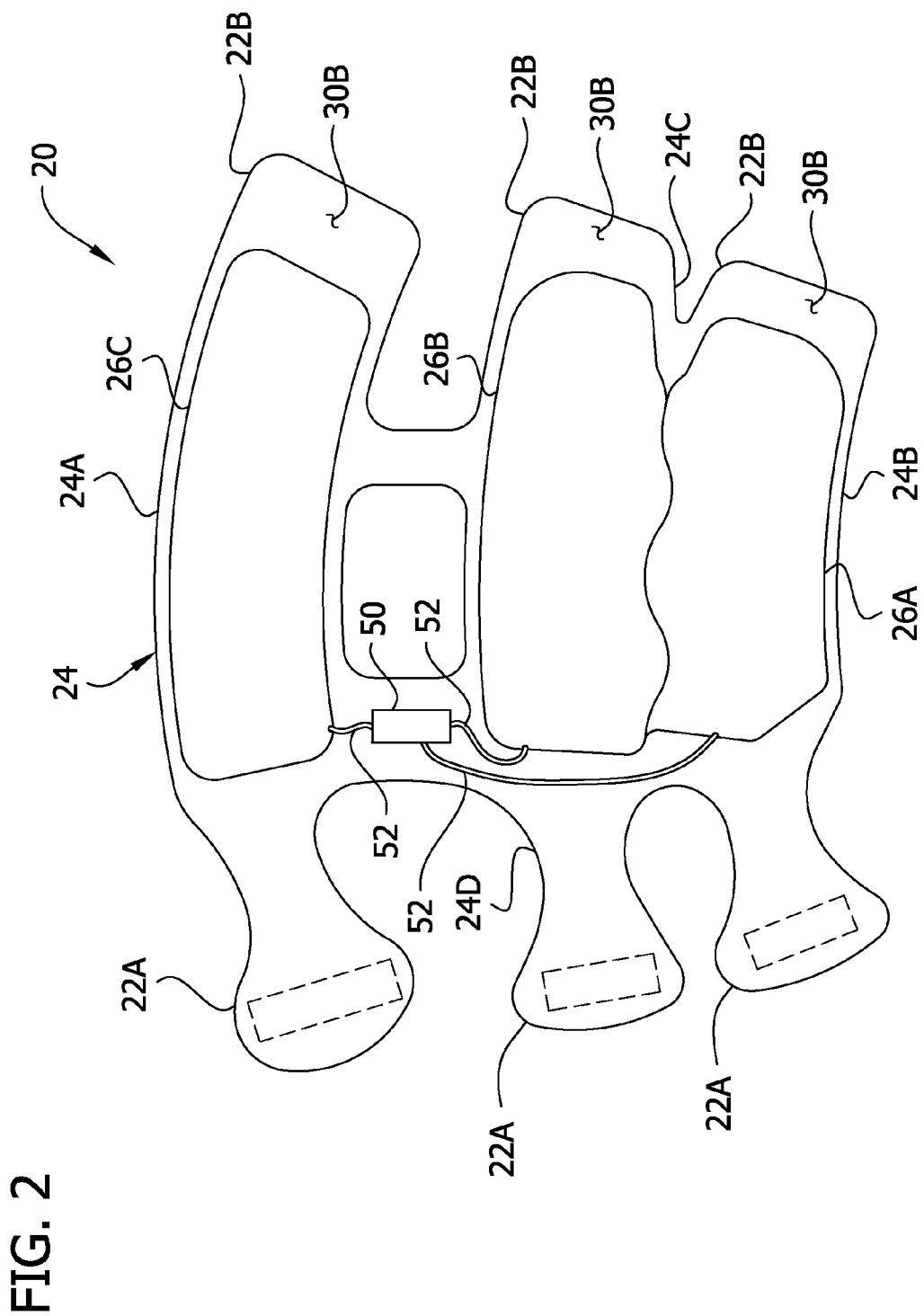
FIG. 2 is a schematical rear elevation of the compression garment.
Figure 3:
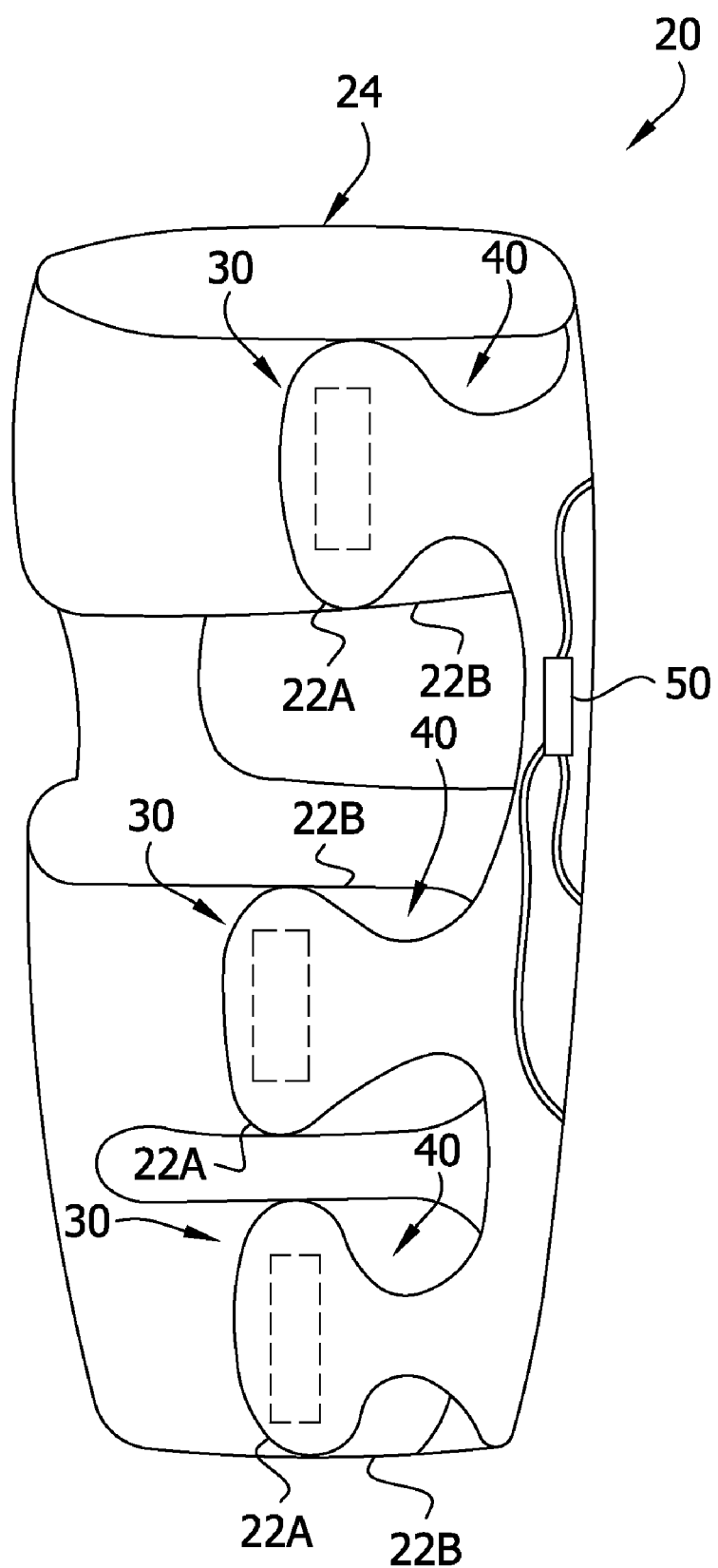
FIG. 3 is a schematical side perspective of the compression garment in a wrapped configuration.

Referring to the drawings and in particular to FIGS. 1-3, a compression garment for applying compression therapy to a body part of a wearer is generally indicated by the reference number 20. The compression garment 20 is adapted for placement on the body part (e.g., a leg or arm). The illustrated compression garment 20 is adapted for placement on a leg. The compression garment 20 may be used to provide compression therapy such as constant or intermittent compression to the body part.

The compression garment 20 includes a flexible wrap, generally designated by 24, and three bladders 26A-26C. The wrap 24 is configured for holding the bladders 26A-26C for compressing the leg while the wrap is in a self-retaining configuration on the leg (e.g., FIG. 3). The wrap 24 has a proximal end 24A sized for wrapping around a proximal portion of the leg, a distal end 24B opposite the proximal end for wrapping around a distal portion of the leg, and lateral side edges 24C, 24D extending between the proximal end and the distal end.

The illustrated compression garment 20 has a "thigh length" size, i.e., the compression garment extends generally from the ankle to the thigh. The bladders 26A-26C include a conventional inflatable chamber and a port in fluid communication with the chamber for selectively delivering fluid from a fluid source to the chamber to inflate the chamber and compress the leg. The bladders 26A-26C are positioned on the wrap 24 to generally overlie the rear side of the leg, and more particularly, the ankle, calf, and thigh, respectively. The three bladders 26A-26C are arranged to lie in sequence along the leg. Other sizes and shapes of garments 20 (e.g., "knee length," extending generally from the ankle to below the knee) or having different configurations of bladders 26A-26C (e.g., one, two, or more bladders) are within the scope of the present invention.

Flaps 22A and 22B extend from respective side edges 24C, 24D and define three sets of corresponding flaps spaced from each other. The flaps 22A, 22B facilitate tightening and securing of the compression garment about the leg. In use, the flaps 22A overlap the corresponding flaps 22B. Thus, flaps 22A and 22B may be referred to as outer and inner flaps, respectively. The compression garment 20 is placed in the self-retaining configuration on the leg by positioning the bladders 26A-26C over desired compression zones on the leg and wrapping the wrap 24 around the leg such that the outer flaps 22A overlap the inner flaps 22B. The compression garment 20 is tightened around the leg by increasing the overlap of the inner and outer flaps 22A, 22B. In the self-retaining configuration, the proximal end 24A is wrapped around the proximal portion of the leg, the distal end 24B is wrapped around the distal portion of the leg, and the lateral side edges 24C, 24D extend generally longitudinally along the leg between the proximal end and the distal end. A generally tight or snug fit is desirable so that when the bladders 26A-26C are pressurized the leg is compressed.

Figure 4:
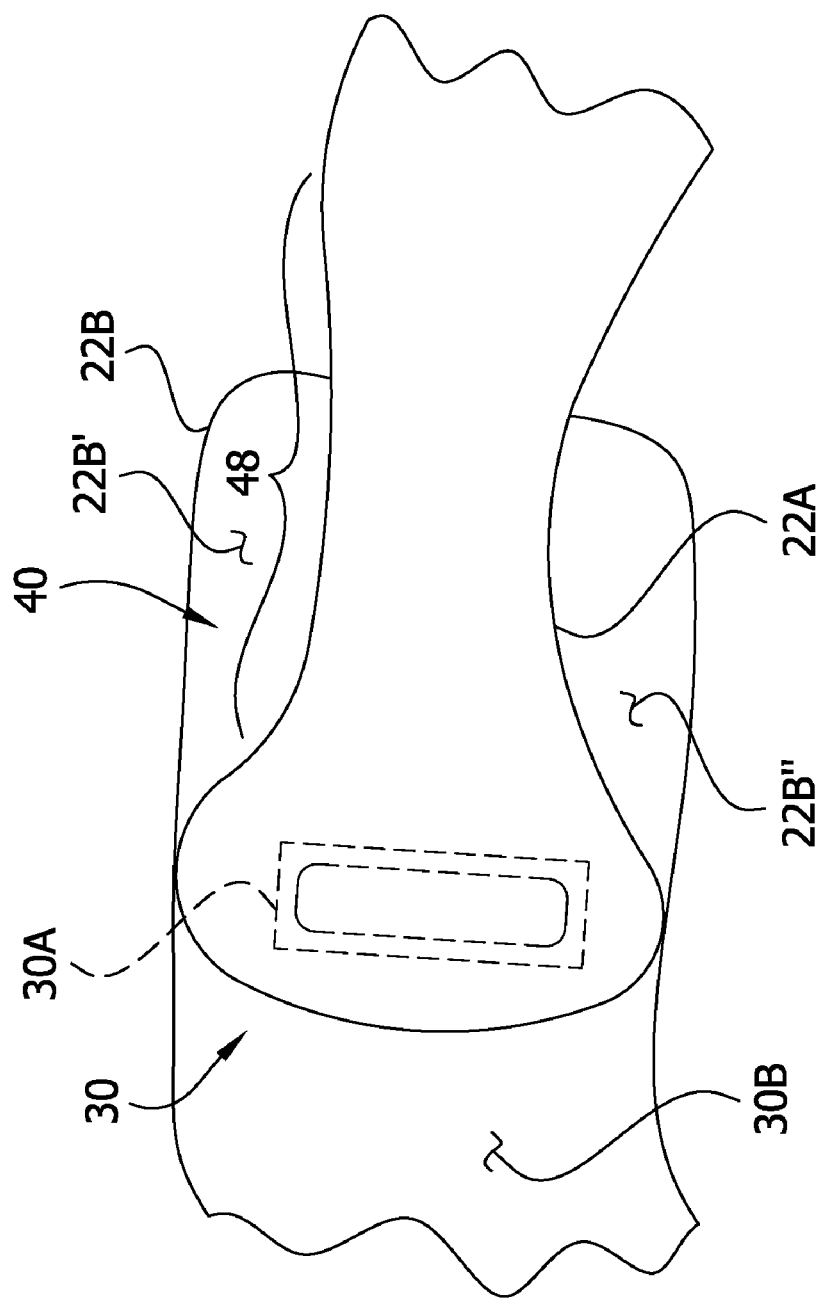
FIG. 4 is a schematical fragmentary elevation of flaps of the compression garment in an overlapped configuration.

Referring to FIGS. 3 and 4, fasteners 30 on the wrap 24 are used to secure the free ends of the outer flaps 22A on the compression garment 20. In the illustrated embodiment, the fasteners 30 comprise hook fabric 30A on the free end of the outer flaps 22A. The fasteners 30 also comprise loop fabric 30B on an outside surface of the inner flaps 22B. Thus, the fasteners 30 are two-part fasteners. Other types of fasteners may be used without departing from the scope of the present invention.

The flaps 22A, 22B are constructed to provide grips, generally designated by 40, on the inner flaps when the outer flaps overlap the inner flaps. Such a construction facilitates gripping of the inner flaps 22B by fingers of a person to tighten the wrap 24 about the body part and hold the wrap in the tightened configuration as the outer flaps 22A are fastened to the inner flaps. The inner flaps 22B each have lengths extending from the respective side edge of the wrap 24C to a free end of the flaps. As shown in FIG. 1, the inner flaps 22B each have a maximum width 42 measured generally perpendicular to a median circumferential centerline 43 of the inner flaps. As illustrated, the width of the inner flaps 22B may be substantially constant along the length of the inner flaps 22B. The outer flaps 22A each have a length extending from the respective side edge of the wrap to a free end of the flaps. The outer flaps 22A each have a maximum width 44 measured generally perpendicular to a median circumferential centerline 45 of the outer flaps, and a minimum width 46 measured generally perpendicular to the centerline 45 of the outer flaps.

The inner and outer flaps 22A, 22B may have various widths. In the illustrated embodiment, the minimum width of the outer flaps 46 is less than the maximum width of respective inner flaps 42. The maximum width of the outer flaps 44 is at least about half as wide as the maximum width of the inner flaps 42. The maximum width of the inner flaps 42 may be about equal to the maximum width of the outer flaps 44.

The outer flaps 22A have proximal and distal edges that are concave or indented defining necks 48 on the outer flaps. In other embodiments, the necks 48 may be defined by only one of the proximal or distal edges of the outer flaps being concave or indented. Embodiments in which proximal or distal edges have concave edges or indentations other than illustrated herein do not depart from the scope of the present invention. The minimum width of the outer flaps 46 occurs at the necks 48. The maximum width of the outer flaps 44 is positioned on the outer flaps 22A closer to the free end of the outer flaps than the minimum width 46 or the neck 48. In the illustrated embodiment, the width of the outer flaps 22A constantly changes along the length of the outer flaps.

The construction of the corresponding flaps 22A, 22B described above defines the grips 40 on the inner flaps 22B when the outer flaps 22A overlap the inner flaps. The grips 40 facilitate tightening the wrap 24 around the leg and holding the wrap in the tightened configuration as the outer flaps 22A are fastened to the inner flaps 22B. One of the grips 40 is shown in more detail in FIG. 4, which shows a fragmentary elevation of a single outer flap 22A overlapping a corresponding inner flap 22B. When the outer flap 22A overlaps the inner flap 22B, at least a portion of the inner flap is not overlapped by the outer flap and is accessible adjacent the neck 48 to facilitate gripping of the inner flap by fingers of a person to tighten the wrap 24 about the body part. More specifically, two portions of the inner flap 22B', 22B" are accessible, one portion 22B' adjacent the proximal edge of the neck 48 and one portion 22B" adjacent the distal edge of the neck. The two accessible portions 22B'; 22B" are spaced from one another by a distance sufficient to receive a segment such as the neck 48 of the outer flap 22A therebetween. The exposed portions of the inner flap 22B', 22B" form the grip 40 for grasping the inner flap 22B when fastening the fastener 30 to secure the wrap 24 in the self-retaining configuration.

The compression garment 20 may be constructed in various ways known in the art. In one construction, the garment 20 is formed from opposing inner and outer sheets of a generally flexible, fluid impervious material (e.g., PVC) that are welded together along bladder weld lines to form the bladders 26A-26C. Alternatively, the bladders 26A-26C may be formed separately and mounted on the compression garment 20.

As shown in FIG. 2, the compression garment 20 may include a pressurizer 50 operatively connectable to the ports of the bladders 26A-26C such as by conduits 52 for inflating the bladders. The illustrated pressurizer 50 is mounted on the compression garment 20. An embodiment in which a pressurizer is removably mounted on a compression garment and operatively connected to bladders on the compression garment is disclosed in more detail in U.S. patent application Ser. Nos. 12/241,670 and 12/241,936, both of which are both assigned to Tyco Healthcare Group LP and hereby incorporated by reference in their entireties. Other embodiments, such as where the pressurizer 50 is not configured for mounting on the compression garment 20 are envisioned as being within the scope of the present invention.

The pressurizer 50 may be programmed to execute various compression regimens, which may include inflation and vent phases. In some regimens, the pressurizer may pressurize one or more of the bladders 26A-26C to a constant pressure for an extended time period. The pressurizer 50 may also intermittently or cyclically pressurize the bladders 26A-26C. Other types of compression regimens are within the scope of the present invention.

In a cycle of use, the compression garment 20 is placed on a body part such as the leg, with the bladders 26A-26C covering or overlying desired target compression zones. The wrap 24 is wrapped around the body part such that outer flaps 22A overlap corresponding inner flaps 22B. A person grips one of the inner flaps 22B by grasping the respective grip 40 using, for example, fingers such as a thumb and a forefinger. While gripping the flap 22B using the grip 40, at least one of the corresponding flaps 22A, 22B is moved with respect to the other of the flaps tending to increase the overlap of the flaps to tighten the compression garment 20 around the leg. The outer flap 22A is fastened to the outside surface of the inner flap 22B using the fastener 30 to secure the garment 20 in the self-retaining configuration on the body part. The outer flap 22A does not overlap the grip 40 when fastened to the inner flap 22B. These steps are repeated for each set of corresponding flaps 22A, 22B. The grips 40 thus facilitate tightening of the compression garment 20 on the leg and holding of the inner flaps 22B in place while the outer flaps 22A are fastened to the outer surface of the inner flaps 22B. The tightened compression garment 20 results in an improved fit for improved compression therapy.

Having described the invention in detail, it will be apparent that modifications and variations are possible without departing from the scope of the invention defined in the appended claims.

When introducing elements of the present invention or the preferred embodiments(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A compression garment adapted for placement on a body part in a self-retaining configuration for providing compression therapy to the body part, the compression garment comprising:

a flexible wrap having a proximal end sized for wrapping around a proximal portion of the body part, a distal end opposite the proximal end for wrapping around a distal portion of the body part, and side edges extending between the proximal end and the distal end;

a bladder held in use by the wrap for compressing the body part, the bladder having an inflatable chamber and a port in fluid communication with the chamber for selectively delivering fluid from a fluid source to the chamber to inflate the chamber and compress the body part;

an inner flap extending from one of said side edges and an outer flap extending from another of said side edges, the outer flap overlapping the inner flap when the garment is in use on the body part; and a fastener attached to at least one of the inner flap and the outer flap for securing the wrap in said self-retaining configuration on the body part in which the proximal end is wrapped around the proximal portion of the body part, the distal end is wrapped around the distal portion of the body part, and the outer flap overlaps the inner flap;

wherein the inner flap has a length extending from the respective side edge of the wrap to a free end and a maximum width measured generally perpendicular to a median circumferential centerline of the inner flap; and wherein the outer flap has a length extending from the respective side edge of the wrap to a free end, a maximum width measured generally perpendicular to a median circumferential centerline of the outer flap that is at least about half as wide as the maximum width of the inner flap, and a minimum width measured generally perpendicular to the median circumferential centerline of the outer flap that is less than the maximum width of the inner flap so that a portion of the inner flap is exposed when the proximal end is wrapped around the proximal portion of the body part, the distal end is wrapped around the distal portion of the body part, and the outer flap overlaps the inner flap forming a grip for grasping the inner flap when fastening the fastener to secure the wrap in said self-retaining configuration on the body part.

2. A compression garment as set forth in claim 1 wherein the maximum width of the outer flap is positioned on the outer flap closer to the free end than the minimum width is positioned.

3. A compression garment as set forth in claim 2 wherein the grip is two portions of the inner flap, the two portions being spaced from one another by a distance sufficient to receive a segment of the outer flap therebetween.

4. A compression garment as set forth in claim 1 wherein the maximum width of the inner flap is about equal to the maximum width of the outer flap.

5. A compression garment as set forth in claim 1 wherein the fastener is a two-part fastener, a first part of the fastener being attached to the outer flap and a second part of the fastener being attached to the inner flap adjacent the grip, permitting the first part of the fastener to be fastened to the second part of the fastener without lapping the first part of the fastener over the grip.

6. A compression garment as set forth in claim 1 wherein the inner and outer flaps are a first pair of corresponding flaps, the compression garment further comprising second and third pairs of corresponding flaps spaced distally from said first pair of corresponding flaps by respective first and second distances, and wherein said grip is a first grip and the garment further comprises second and third grips associated with the second and third pairs of corresponding flaps, respectively.

7. A compression garment adapted for placement in a self-retaining configuration on a body part for imparting compression therapy on the body part, the compression garment comprising:
a flexible wrap having a proximal end sized for wrapping around a proximal portion of the body part, a distal end opposite the proximal end for wrapping around a distal portion of the body part, and first and second side edges extending between the proximal end and the distal end;
a bladder held in use by the wrap for compressing the body part, the bladder having an inflatable chamber and a port in fluid communication with the chamber for selectively delivering fluid from a fluid source to the chamber to inflate the chamber to compress the body part;
an inner flap extending from one of said side edges and an outer flap extending from another of said side edges, the outer flap overlapping the inner flap when the garment in use on the body part; and
a fastener attached to at least one of the inner flap and the outer flap for securing the wrap in said self-retaining configuration on the body part in which the proximal end is wrapped around the proximal portion of the body part, the distal end is wrapped around the distal portion of the body part, and the outer flap overlaps the inner flap;
wherein the inner flap has a length extending from the respective side edge of the wrap to a free end and a maximum width measured generally perpendicular to a median circumferential centerline of the inner flap; and
wherein the outer flap has a length extending from the respective side edge of the wrap to a free end, a maximum width measured generally perpendicular to a median circumferential centerline of the outer flap that is at least about half as wide as the maximum width of the inner flap, and a neck having a width less than the maximum width of the outer flap, the maximum width of the outer flap being positioned on the outer flap closer to the free end than the neck is positioned such that when the outer flap overlaps the inner flap at least a portion of the inner flap is not overlapped by the outer flap and is accessible adjacent the neck to facilitate gripping of the inner flap by fingers of a person to tighten the wrap about the body part.

8. A compression garment as set forth in claim 7 wherein when the outer flap overlaps the inner flap first and second portions of the inner flap are not overlapped by the outer flap, the first and second portions being longitudinally offset with respect to the neck whereby the first portion is accessible adjacent a proximal edge of the neck and the second portion is accessible adjacent a distal edge of the neck.

9. A compression garment as set forth in claim 7 wherein the width of the neck is less than the maximum width of the inner flap.

10. A compression garment as set forth in claim 9 wherein the maximum width of the inner flap is about equal to the maximum width of the outer flap.

11. A compression garment as set forth in claim 7 wherein the width of the inner flap is substantially constant along the length of the inner flap.

12. A compression garment as set forth in claim 7 wherein the outer flap comprises proximal and distal edges extending between the respective side edge and the respective free end, and at least one of the proximal and distal edges is generally concave.

13. A compression garment as set forth in claim 12 wherein the proximal edge and the distal edge of the outer flap are generally concave.

14. A compression garment as set forth in claim 7 wherein the outer flap comprises proximal and distal edges extending between the respective side edge and the respective free end, and at least one of the proximal and distal edges of the outer flap is indented.

15. A compression garment as set forth in claim 14 wherein the proximal edge and the distal edge of the outer flap are indented.

16. A compression garment as set forth in claim 7 wherein the width of the outer flap constantly changes along the length of the outer flap.

17. A compression garment as set forth in claim 7 wherein at least a portion of the fastener is attached to the outer flap and is positioned closer to the free end than the neck is positioned.

18. A compression garment as set forth in claim 7 wherein the inner and outer flaps are a first pair of corresponding flaps and the compression garment further comprises second and third pairs of corresponding flaps having substantially the same construction as the first pair of corresponding flaps and being spaced longitudinally from the first pair of corresponding flaps.

19. A method of placing a compression garment on a body part for providing compression therapy to the body part, the compression garment including a bladder having an inflatable chamber and a port for providing fluid to the inflatable chamber, the method comprising:
wrapping the compression garment around the body part such that an inner flap of the compression garment is overlapped by an outer flap of the compression garment;

gripping the inner flap by grasping a portion of the inner flap;

while gripping the inner flap, increasing the overlap of the outer flap with respect to the inner flap to tighten the compression garment around the body part; and securing the outer flap to the inner flap when the garment is tightened around the body part and without overlapping the grip with the outer flap.

\* \* \* \* \*